United States Patent [19]

Vaillancourt

[11] Patent Number: 4,652,256
[45] Date of Patent: * Mar. 24, 1987

[54] CLOSED SYSTEM CATHETER WITH GUIDE WIRE

[75] Inventor: Vincent L. Vaillancourt, Livingston, N.J.

[73] Assignee: Manresa, Inc., Hillsdale, N.J.

[*] Notice: The portion of the term of this patent subsequent to Jun. 25, 2002 has been disclaimed.

[21] Appl. No.: 792,457

[22] Filed: Oct. 29, 1985

[51] Int. Cl.$^4$ .................... A61M 5/00; A61M 25/00
[52] U.S. Cl. ...................................... 604/52; 604/164; 604/168; 604/171
[58] Field of Search ............... 604/220, 164, 163, 171, 604/165, 168, 52, 170; 128/658

[56] References Cited

U.S. PATENT DOCUMENTS

| | | | |
|---|---|---|---|
| 3,757,771 | 9/1973 | Ruegg et al. | 604/163 X |
| 3,825,001 | 7/1974 | Bennet et al. | 604/171 X |
| 3,903,885 | 9/1975 | Fuchs | 604/165 X |
| 4,046,144 | 9/1977 | MacFarlane | 604/168 |
| 4,326,520 | 4/1982 | Alley | 604/163 X |
| 4,417,886 | 11/1985 | Frankhouser et al. | 604/164 X |

Primary Examiner—Stephen C. Pellegrino
Attorney, Agent, or Firm—Ralph R. Roberts

[57] ABSTRACT

A catheter system is provided for the introduction and placement of a flexible catheter into the lumen of an artery or vein. A guide wire is provided and is kept in a sterile condition within a flexible bag-like enclosure attached to the hub of a needle. The needle is hollow and is sharpened in the usual manner and is secured in a hub to provide a needle assembly. This hub is provided with a skirt and extends through this hub and into flow communication with a "flashback" chamber. In one embodiment, the needle has a side transverse hole in its interior end, and in another embodiment the needle's inner end is in flow communication with a tapered recess in the needle hub which provides a guideway for the guide wire which, when it enters the needle, prevents blood flow. The guide wire is manipulated forwardly by grasping the wire through the bag-like enclosure and advanced forwardly by "feel" and into the lumen after penetration has been made as indicated by the "flashback." The catheter is separated from the needle hub and advanced along the guide wire until placement is achieved, after which the needle, guide wire and bag are withdrawn from the patient and discarded.

29 Claims, 6 Drawing Figures

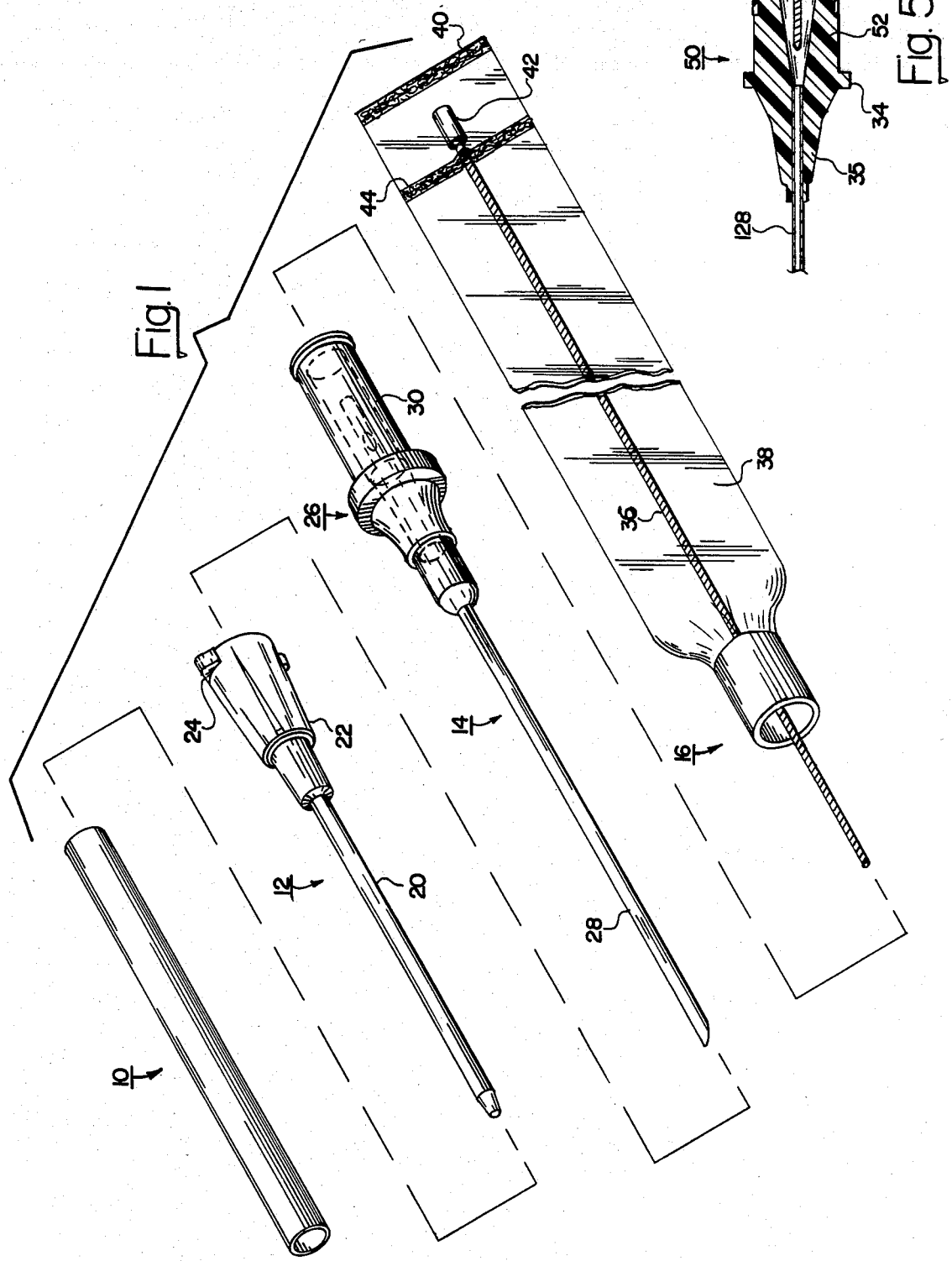

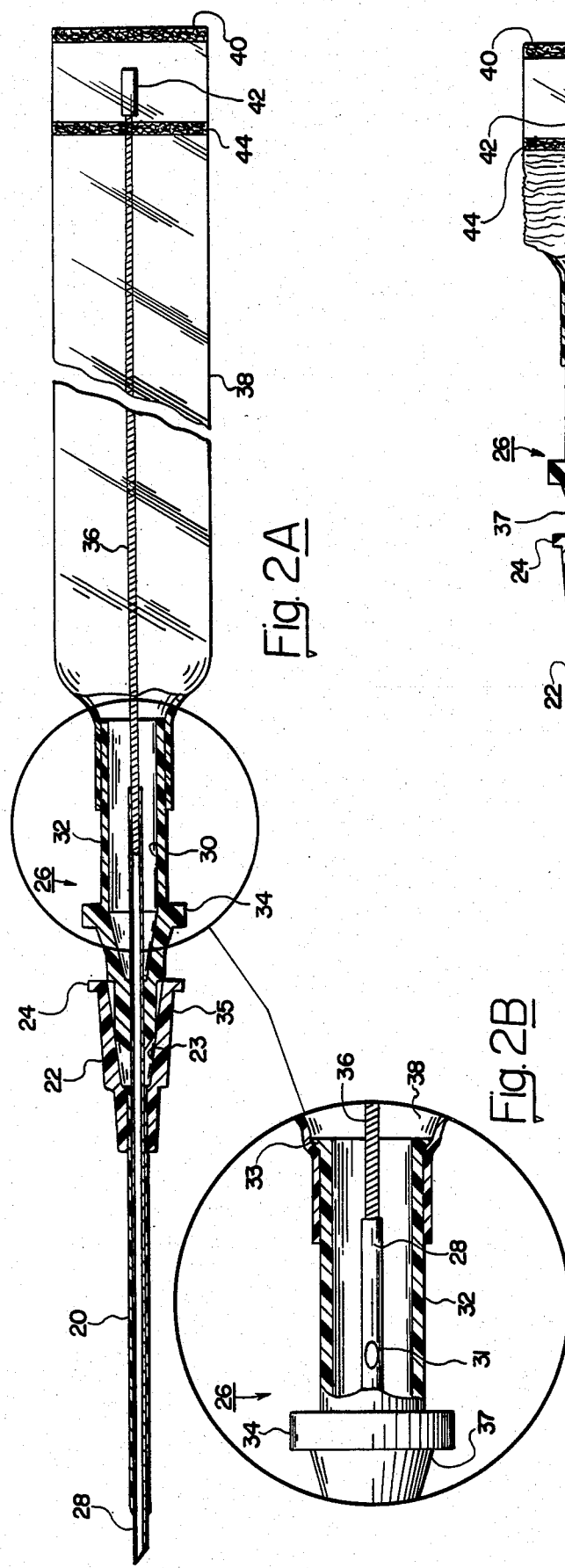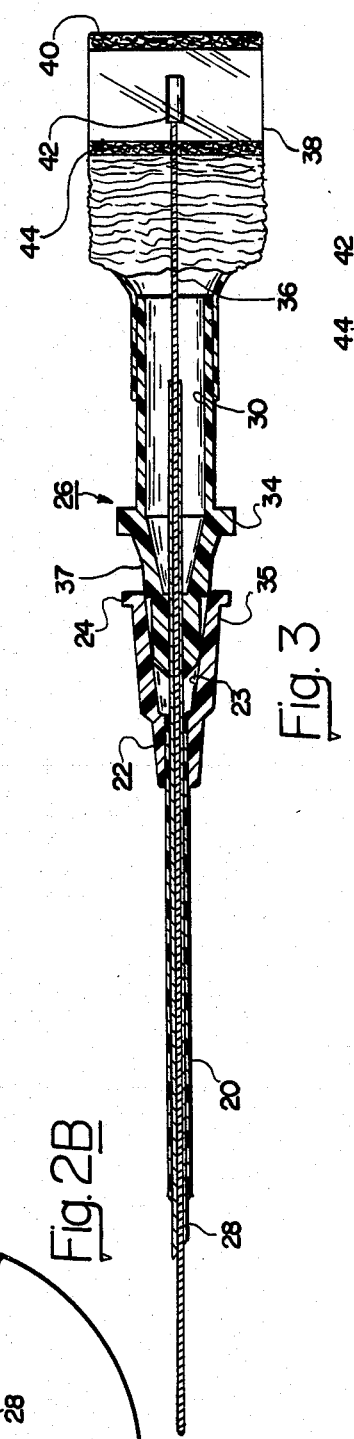

CLOSED SYSTEM CATHETER WITH GUIDE WIRE

CROSS-REFERENCE TO RELATED PATENTS

This application pertains to a closed system catheter with guide wire as shown in the patent having Ser. No. 518,122 and filed July 28, 1983. This application matured as U.S. Pat. No. 4,525,157, issuing June 25, 1985. To the extent applicable, this patent is incorporated by reference into this application.

BACKGROUND OF THE INVENTION

1. Field of the Invention

With reference to the classification of art as established in and by the United States Patent Office, this invention is believed to be found in the field pertaining to "Surgery" and particularly to "flexible catheter guide."

2. Description of the Prior Art

Arterial blood infusion and withdrawal devices are known and the technique of a guide wire inserted into the lumen of the artery is known and shown as prior art in FIGS. 1 A through 1 C to be hereinafter more fully discussed. A catheter placement system is shown in U.S. Pat. No. 3,416,531 to EDWARDS, as issued Dec. 17, 1968; a guide for the catheter is also shown in U.S. Pat. No. 3,547,103, as issued to COOK on Dec. 15, 1970; a flash-back indicator is shown in U.S. Pat. No. 3,942,514, as issued to OGLE on Mar. 9, 1976; a withdrawal system using a guide wire is shown in U.S. Pat. No. 4,006,743, as issued to KOWARSKI on Feb. 8, 1977; a cetheter placement assembly is shown in U.S. Pat. No. 4,046,144 to MC FARLANE, as issued Sept. 6, 1977; an extraction device is shown in U.S. Pat. No. 4,215,702, as issued to MAYER on Aug. 5, 1980; a blood collecting device with indicator is shown in U.S. Pat. No. 4,154,229, as issued to NUGENT on May 15, 1979; a needle and sheath are shown in U.S. Pat. No. 4,230,123, as issued to HAWKINS, Jr. on Oct. 28, 1980, and a guide wire placement is shown in U.S. Pat. No. 4,274,408, as issued to NIMROD on Jan. 23, 1981.

Of particular note is U.S. Pat. No. 4,417,886 to FRANKHOUSER et al, as issued Nov. 29, 1983. In this patent, in addition to Hawkins and Nimrod noted above, are referenced U.S. Pat. No. 3,995,628 to GULA; U.S. Pat. No. 4,068,659 to MOOREHEAD; U.S. Pat. No. 4,068,660 to BECK; U.S. Pat. No. 4,205,675 to VAILLANCOURT; and U.S. Pat. No. 4,306,562 to OSBORNE. In the Frankhouser disclosure, it is particularly noted the necessity of using an elongated tubular member connected to and projecting rearwardly from the proximal end of the needle. This tubular member is of a transparent, semi-rigid plastic material. Although the plastic material may have some flexibility, it should have sufficient resilience so that it maintains its tubular configuration in use. This disclosure continues: "In its preferred form, tubular member has a longitudinally extending slot running from a point adjacent the needle hub." An extending handle is adapted to be moved in this slot in the tubular member, with this handle attached to the guide wire to produce the desired movement. The Frankhouser showing does not employ an arrangement which would lend itself to or suggest a closed system with product sterility being maintained after removing the outer package or during advancement of the guide wire in the catheter.

Although the present apparatus may be used in both veins and arteries, penetration into the artery is the most difficult and requires the greater expertise. The preferred arterial catheter insertion site is the radial artery immediately proximal to the wrist. This site is preferred because the artery is relatively close to the skin and therefore relatively accessible. The position and orientation of the artery is normally located by detecting the pulse and following the pulse beat up the artery for about one inch or more in length. Some practioners draw an ink line on the skin to show this position and orientation. The catheter and needle assembly is then introduced at an angle about thirty to forty-five degrees to the surface of the skin, with the bevel of the needle facing up, or toward the outer surface.

This method of insertion is a real challenge even to the most experienced practitioner. First, he must find the artery with the point of the introducer needle and obtain flashback through the hollow of the introducer needle. Many practitioners remove the existing flash plugs in hopes of being able to obtain a quicker flashback (indication of piercing the artery). These practitioners desire a quicker flashback in the hope that this will indicate entry into the artery before penetration through the back wall of said artery with the needle point.

The artery wall is both thick (to support arterial blood pressure) and elastic and as a result the needle significantly compresses or dimples the artery wall before penetration is achieved. When the needle finally penetrates the first wall the pressure in the artery causes the wall to pop back along the needle, leaving minimal resistance to further forward travel of the needle. The most common occurrence is for the point of the needle to bury itself in the back wall of the artery when the first wall of the artery "pops" back over the heel of the bevel and along the shank of the needle. To compensate for this, some practitioners actually twist the introducer needle about its axis after they have observed flash in the introducer hub. This maneuver is intended to orient the main bevel angle parallel to the back wall of the artery and lift the embedded point out of the back wall. Other practitioners tend to draw the introducer needle back after they see flashback on the assumption that the point is embedded into the back wall of the artery.

Once the practitioner has observed flashback in the introducer and has been able to slide the catheter forward a short distance on the introducer, he assumes that he is in the artery with the tip end of the catheter. At this point, however, it is not just a simple matter of sliding the entire assembly or the catheter alone up the artery as the axis of the introducer needle is disposed at a substantial angle to the axis of the artery. This needle, when and as positioned, cannot be advanced up an artery or vessel. Rather, the practitioner utilizes a delicate feel to slide the catheter off of the introducer needle and into and up the artery. This procedure requires the advancing catheter to bend at its point of entry into the artery. Many times the catheter becomes embedded in the wall of the artery and the practitioner must detect this problem by the feel of the catheter as the catheter is slid forward. If the practitioner does not follow this procedure a substantial risk of gouging the lining of the artery and inducing a severe thrombosis occurs.

In order to get the catheter into the artery the catheter is bent so as to follow the artery. At this point the practitioner usually retracts and readvances the introducer several times during each insertion and puncture of the artery. Each placement may entail half a dozen unsuccessful attempts. Each failed attempt further aggravates the problem, because the artery goes into "spasm." After a few unsuccessful attempts, the user gives up using the catheter unit in the started attempt and with a fresh new unit begins again. In a sampling of hospitals it was found that over two needle-catheter units were used to achieve each successful catheter placement as a further indication of how difficult it is to successfully place catheters in the artery.

SUMMARY OF THE INVENTION

This invention may be summarized, at least in part, with reference to its objects. It is an object of this invention to provide, and it does provide, a novel and improved needle inserting device for gaining access to blood vessels, particularly arteries. The needle is hollow and is carried within a catheter secured to a hub. The needle is secured to this hub and carries within its bore a guide wire that is selectively movable. The guide wire is retained within a flexible bag so that contamination is excluded.

It is a further object of this invention to provide, and it does provide, a needle within a catheter, said needle having a sharpened entering point by which penetration of a vessel may be and is achieved. The needle is tubular and at its rear end discharges into a flashback (clear or translucent hub) indicator. A flexible and impervious bag is secured to the hub carrying the needle and enclosing the guide wire so that a sterile field of environment is provided and the guide wire may be moved into the blood vessel without a need for gloves, mask, gowning, etc., under aseptic conditions and contamination-free.

It is a further object of this invention to provide, and it does provide, an improved needle and catheter in which the catheter is carried by a hub and the needle is carried by a separate hub that is separable from the catheter hub. This needle is tubular and is disposed to carry a guide wire attached to the rear end of the flexible and impervious bag. This restraint provides means to prevent unwanted movement of the wire while still providing manipulative (advancement) movement of the wire within the needle and/or catheter. The needle is adapted for conducting blood, after penetration of the vessel, so that an immediate flashback is detected. The guide wire is carried within and is manipulated while in a flexible and closed lay-flat tubular bag attached to the needle hub.

The prior art devices do not provide and maintain a sterile environment during manipulative use of the guide wire to place the catheter in a vein or artery. In particular, the Frankhouser patent, identified above, has the guide wire manipulated and advanced by a handle which is moved in and along a slot. As to be more fully disclosed and shown, the guide wire of Applicant's device is advanced by gripping the guide wire between the thumb and fingers of the user and advancing same into the vessel.

As far as is known, this closed system catheter with guide wire has advantages over prior products and among other advantages include: (1) providing a catheter introduction system which has all the "feel" advantages of a "typical" Intravenous Catheter, (2) providing an entry point for a guide wire without blood leakage, (3) the advancement of the guide wire into the blood vessel under closed system (sterile) conditions, (4) the sizing by the needle of the entrance opening to the blood vessel sufficient to allow the movement of the catheter into it, (5) the advancement of the catheter into the vessel under conditions that will not injure the vessel wall and being positively guided as to where it should go, and (6) the removal of all components other than the catheter which remains in place in a sterile manner maintaining a closed system until the moment of hook-up to the pressure monitoring system, administration set, etc.

This embodiment also provides a product which is neither bulky nor cumbersome and therefore allows the practitioner to maintain control of the insertion process through "feel," which is a very vital part of any blood vessel (especially artery) entering procedure. This "feel" is achieved by (1) minimizing the lumen of the device, (2) providing a flexible end (bag and wire guide) which also maintains good balance in the device, and (3) allowing the practitioner to "feel" the wire guide as it is advanced. For this reason, the guide wire is grasped or gripped by the user, preferably using a thumb and digit. Said guide wire is gripped through the bag which is very thin and supple and does not appreciably alter the user's sense of "feel." Advancement is by gripping the guide wire through the bag and intermediate the ends of the wire. The guide wire is usually grasped about an inch from the needle hub and advanced (moved forwardly) in small increments in and with repeated steps until the guide wire advancement limit or extent is reached.

In brief, there is depicted a flexible catheter having a selected bore. The entering end of the catheter is chamfered for easy entrance of the catheter into a body opening and then into a penetrated blood vessel (artery or vein). The hub carrying the catheter has a tapered recess for receiving the male luer connector of an administration set such as is used in arterial pressure monitoring. A needle is disposed within and axially aligned with the catheter. The sharpened end extends beyond the catheter to effect penetration. The opposite end is secured to a plastic hub. This needle hub has its outer end portion sized and shaped to be retained within the socket in the catheter hub. The needle has its discharge end protruding through the back end wall and is adapted to provide a flashback indicator when the sharp needle end penetrates a vessel carrying blood.

A wire guide is provided with means for advancing this wire through the needle and then into the lumen, said wire bending to the configuration and path of the lumen. The guide wire is carried in a closed and flexible sheath or lay-flat tube that prevents contamination of the wire and the pathway into the vessel. This flexible sheath is secured to the needle hub. The guide wire may be color-coded to show placement advance of the guide wire to the end of the needle.

In the drawings and embodiments as shown and described in this invention, the use of an additional centering plug as in the referenced U.S. Pat. No. 4,525,157 is not used. In this invention, the guide wire is advanced into the needle without the provision of a separate member providing a centering plug. In one embodiment, the guide wire is already in a rearwardly-extending portion of the needle carried in a hub. Blood flow indication is provided by a small hole formed in a side wall of said needle. In the alternate embodiment, a tapered guide is provided in the needle-retaining hub and the guide wire is adapted to enter and advance through the needle bore.

After penetration of the vessel by the needle end and a flashback is perceived, the guide wire is first advanced to the end of the needle and then by careful manipulation is further advanced into the vessel. After the desired advancement into the vessel, the guide wire is used to allow the catheter to be slid along the guide wire generally before the needle is withdrawn from the body opening. The hub of the catheter is separated from the hub of the needle and then said needle, with guide wire and bag, is discarded, leaving the catheter in place in the artery or vein.

In the embodiments to be shown and more fully described hereinafter, it is to be noted that the guide wire has its rear end secured to the terminal or distant end of the bag so that with grasping and manipulating of the guide wire by a thumb and finger of the user, an advancing of the guide wire results in an accordion-like condition of the bag. This bag is made of a lay-flat plastic tubing generally about one- to two-thousandths of an inch in thickness and having no rigidity. This bag is of transparent plastic much like that used for a wrap of sandwiches, etc. The guide wire used in this device is sufficiently flexible to easily follow a vein or artery and therefore in the smaller catheter sizes generally cannot be advanced by grasping the distal end, but must be advanced by manipulation by the practitioner. This bag, while protecting the guide wire and other elements and maintaining sterility, allows the practitioner to manipulate the guide wire and establish a feel of the advancing guide wire substantially as if the bag was absent. This procedure or practice has not been available in the known prior art devices.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen embodiments of closed catheter systems with a catheter and a guide wire for placement in a lumen as adopted for use in penetration of a lumen and showing a preferred means for bending and advancing a catheter by use of a guide wire. These specific embodiments have been chosen for the purpose of illustration and description as shown in the accompanying drawings wherein:

BRIEF DESCRIPTION OF THE DRAWINGS

FIG. 1 represents an exploded isometric view of the components as used for the catheter with guide wire of this invention;

FIG. 2 A represents a sectional side view, partly diagrammatic, of the device of FIG. 1 as assembled and ready for use in a patient;

FIG. 2 B represents a sectional view, partly fragmentary, of the needle hub and secured needle, this view in an enlarged scale to illustrate a hole formed in the side of the rearwardly-extending needle;

FIG. 3 represents the sectional side view of the device of FIG. 2 A, but with the guide wire advanced to substantially its extended limit;

FIG. 4 represents the sectional side view of FIG. 2 B, but with the catheter and hub separated from the needle, attached envelope and guide wire, and FIG. 5 represents a sectional side view, partly fragmentary, and showing an alternate construction of a needle secured in a molded hub, this hub having a taper for guiding the entering end of a guide wire.

In the following description and in the claims, various details are identified by specific names for convenience. These names are intended to be generic in their application. Corresponding reference characters refer to like members throughout the several figures of the drawings. Structural details may be modified without departure from the concept and principles of the invention and the invention may be incorporated in other structural forms than shown.

EMBODIMENT OF FIG. 1

In FIG. 1 there is depicted the catheter with guide wire of this invention in an exploded view to illustrate the relationship of components. As shown in this FIG., there is provided a conventional protector 10 which is usually of an extruded plastic. A flexible catheter with a hub is generally identified as 12 and this essential component is also quite conventional. A needle and hub, generally identified as 14, has the hub with at least the rearwardly-projecting skirt portion of a clear or translucent material to provide blood flow or penetration of the lumen. A bag and guide wire is generally identified as 16. The projecting of the needle into the cavity on the needle hub is shown in FIGS. 2 A and 2 B. The lay-flat bag enclosure as depicted has the rear of the guide wire enclosed and retained by heat-sealing means, but this is not a patentable distinction.

EMBODIMENT OF FIG. 2 A

In FIG. 2 A is shown a sectional view of the assembled components of FIG. 1 with the protector 10 removed. This sectional view shows the device ready for use with a patient. A flexible catheter 20 is conventional and is attached to a molded hub 22 with a tapered cavity 23 formed therein. Grasping ear or a flange portion 24 is provided on this hub to provide a luer lock connector. Immediately to the right is a needle hub, generally identified as 26. This needle hub is molded of substantially translucent or clear plastic. A needle 28 of metal (usually stainless steel) is of hollow tubing and is sharpened at the entering end. This needle is secured in the molded hub and extends into the cavity 30 formed in said hub. In this extending portion of the needle 28 and very close to the left or securing wall of the molded hub 26 is a small hole 31 formed in one of the side walls of the needle 28. This hub molding has an elongated tubular skirt 32 usually with a safety edge or end 33 (FIG. 2 B) A flange 34 provides grasping means for manipulation and separation as description hereafter in FIG. 4. This hub 26 is formed with a forward taper 35 adapted to seat snugly in the cavity 23 provided in the catheter hub 22. Within the bag 38 is the guide wire 36 whose entering end is already placed within the needle, but is not forward enough to come in the way of hole 31.

Still referring to FIG. 2 A, it is to be noted that this guide wire 36 is carried within a very supple bag or envelope, now specifically identified as 38, which bag is attached to the rear skirt portion of the needle hub 26 and secured as by a heat-seal, cement or the like. The lay-flat bag 38 is sized to be a slide fit over the lip or rim 33 which is conventionally round. As depicted, this bag is flat until it reaches its distal (right) end whereat it is closed by a heat-seal 40. A second heat-seal 44 is shown by which this protected end of the guide wire 36 is retained in and at this end of the bag. A protector sleeve 42 or the like is provided on the far end of the guide wire to prevent penetration of the bag by a small guide wire end.

EMBODIMENT OF FIG. 2 B

The enlarged view of FIG. 2 B is partly diagrammatic so as to illustrate the construction and use of this needle; needle hub, bag and guide wire. As depicted, needle 28 is fixed in place when hub 26 is molded. This needle is made sufficiently long so as to extend into the skirt 32 of the molded hub and has a hole 31 which is positioned near to the inner end of the molded needle-retaining portion of the hub. This extending portion of the needle terminates within this skirt portion so that a practitioner cannot inadvertently engage this needle during manipulation and advancement of the guide wire. The guide wire 36 is mounted in the needle at the time the end of bag 38 is slid over and secured to the skirt 32 of the hub 26. Penetration of the lumen of the patient causes blood to flow through the needle to the hole 31 and, if not blocked from further advance by the guide wire, the blood would also exit the end of the needle. The placed guide wire 36 insures movement of same through the needle 28 after blood "flashback" is obtained.

EMBODIMENT OF FIG. 3

In FIG. 3 the device is shown with the guide wire 36 extending beyond the needle 28 and catheter 20. It is to be noted that movement of the guide wire is achieved only by grasping the guide wire through the bag 38 near the hub 26. This wire is grasped by the practitioner's thumb and forefinger and usually advanced in small increments or steps. The bag 38 during this formed advancement of the guide wire in the needle 28 is pushed into an accordion-like condition. The length of the guide wire and advancement length are a matter of selection. As noted above, the advancement of the guide wire within the needle effectively halts the flow of blood through the needle. The entering end of the guide wire is formed (blunted) so as to not effect a puncture of the lumen of the patient's vein or artery.

EMBODIMENT OF FIG. 4

In FIG. 4 the device of FIG. 2 A is shown, with the catheter 20 and hub 22 in a substantially separated condition. It is assumed that the guide wire has been advanced to its desired limit, after which the flexible catheter has been advanced along the guide wire into the lumen in the patient. The advancement of the catheter requires disassembly of the catheter and hub from the needle and guide wire and associated components. The withdrawal from the catheter 20 and subsequent discarding of the needle 28, attached hub 26, bag 38 and guide wire 36 allows blood flow through the catheter 20 and hub 22 with its tapered socket 23. Connection to another device or accessory is achieved rapidly.

EMBODIMENT OF FIG. 5

Referring next to FIG. 5, there is shown in a diagrammatic manner an alternate construction to that shown in FIGS. 1, 2 A 2 B, 3 and 4. Rather than having the needle extending into the skirt-enclosed portion and the guide wire initially within the needle, this arrangement provides a variation. The needle 128 is like needle 28, but rather than extend into an enclosure, is terminated at the rear end of the gripping portion of a molded hub identified as 50. Like hub 26 of FIG. 2 A, this molding includes a forward tapered end portion 35 that extends from a manipulating flange portion 34. To the rear of this flange 34, the molded hub has a portion 52 which is shown as having a reduced step portion or shoulder 54 sized to receive and retain the forward end of bag 38 described above. The entering end of guide wire 36 is shown a short distance from the end of needle 128. A guide taper 56 is formed in this molded hub and, in use, the forward movement of the guide wire 36 is such that the guide wire enters the needle and blocks the flow of blood in the needle 128. Conventionally, the hub 50 is of transparent plastic but, even if not, the flow of blood through the needle into the bag would indicate to the practitioner that penetration of the lumen has been made. After this indication, the guide wire is inserted into the needle 128 and advanced as described above in connection with FIG. 3. Separation is made as shown and described in FIG. 4.

USE AND OPERATION

The catheter with guide wire of this invention anticipates the use of a guide wire to advance and position a flexible catheter in the lumen of the patient. As the catheter is comparatively large and not very flexible when compared to the vessel lumen's size, advancement (pushing) into a lumen is often difficult so that a guide wire is used as a guide. After placing the catheter, the rest of the device is discarded.

The catheter and hub are very conventional. The protector cap 10 is made to suit the device which may have catheters from sixteen to twenty-two gauge, with the catheter length and size a matter of selection. The needle is secured in place by the molding of the needle hub, but this is not to preclude the securing of the needle in the molded hub by cement or the like. Blood flow from the penetrated lumen shows the practitioner that further advancement of the needle is not required. The advancement of the guide wire in the needle usually restricts flow of blood into the bag 38 but, if blood does pass by the guide wire 36, it is quite minimal but may be used as an indicator. Bag 38 is made from thin, supple plastic so that the guide wire can be gripped through the side walls of the plastic bag and moved into the lumen. The bag 38 is conventionally made from extruded "lay-flat" plastic tubing having a wall thickness of one- to three-thousandths of an inch. This tubing is sized to go over the outer diameter of the skirt 32 or onto shoulder 54 and be fixedly secured thereto. The needle and guide wire are so selected that the guide wire is easily positioned in the needle 28 without hang-up.

The closing of the distal end of the bag or envelope 38 is usually done by heat-sealing. This closing of the end achieves two purposes. A first purpose is to maintain sterility. Sterilizing is by known and approved means. The other purpose is to retain the guide wire so that this wire is positioned in such a manner that it can readily be advanced through the needle. A single means of retaining this guide wire is shown, but other means may be employed and the configuration of the end closing and wire retention are merely a matter of design. By restraining the end of the guide wire by some bag means, positioning can be positively achieved and unwanted movement eliminated.

It is to be noted that the cannula portion of the needle is hollow and of a selected size to suit the desired use. The catheter has its entering end made as an interference fit to provide a fluid seal. The rest of the catheter is a free slip fit on the shaft of cannula. The cannula and catheter are of a length which has been selected for the particular use desired. The guide wire is of a sufficient length and flexibility to be easily advanced by the practitioner into the lumen of a vessel a desired distance so that the catheter may follow the guide wire and be positioned in the lumen of said vessel.

The above catheter placing system and apparatus provides an improved method for catheter placement using a guide wire for positioning in the lumen of a penetrated vessel. This method for introducing and placing a flexible catheter into the lumen of a vessel such as an artery or vein by a practitioner includes using an advancement of a guide wire into and up said lumen and then over and along said guide wire advancing said catheter, said method including the steps of:

providing a hollow needle of a determined length and sharpening the entering end;

securing and mounting a molded hub to said needle and positioning this hub at a selected distance from the sharpened end of the needle and forming this hub with a skirt portion and providing therewith an interior cavity which is open to the rear and forming the forward end of this hub with a tapering contour;

providing a flexible catheter having a formed through bore sized to be slideable on and along the outer diameter of the needle and forming the entering end of said catheter so as to be easily inserted with the sharpened end of the needle into the lumen of the vessel, and fixedly securing the other end of the flexible catheter in a hub member which is formed so as to be mounted on the contoured forward end of the needle hub;

providing a guide wire of a selected length and having a blunted entering end sized to be a slide fit in the bore of the needle and advancing this wire by manipulation to and through the bore of the needle, and as this wire is advanced it exits the sharpened end of the needle and, with further advancement, the practitioner causes the advancing wire to follow the lumen path of the blood vessel, and providing and securing to the open rear end of the needle hub a flexible enclosure from lay-flat tubing, this tubing of a determined length and at least partially encapsulating the guide wire and retaining the distal end of said guide wire at or near the unsecured end of the tubing and sealing this unsecured end of the tubing.

In the depicted apparatus, the front or entering end of the catheter 20 is shown with an angled contour. This is usually produced by a heated die to insure a tight fit of the catheter on the shank of the needle 28. The securing of the fore end of the bag or envelope 38 to the needle hub 26 is by known means including heat-sealing, cement or by an added shrink-band. The fore end of the envelope is secured in such a manner that the interior of the bag or envelope 38 is sealed and can and is sterilized before shipping and use in a patient. The sealing of the rear end of the envelope 38 also secures the distal end of the wire 36 and many methods of securing may be provided. As depicted, the double heat-seal 40 and 44 not only insures the sealing of the envelope but, with an added sleeve portion 42 secured to the distal end of the wire 36, the inner heat seal, as seen in FIGS. 3 and 4, provides for the retention of the wire during manipulation and separation.

To the extent applicable, the disclosure in U.S. Pat. No. 4,525,157, as issued June 25, 1985, is incorporated by reference into the above application.

Terms such as "left," "right," "up," "down," "bottom," "top," "front," "back," "in," "out" and the like are applicable to the two embodiments shown and described in conjunction with the drawings. These terms are merely for the purposes of description and do not necessarily apply to the position in which the catheter with guide wire may be constructed or used.

While particular embodiments of the apparatus and method of constructing and using have been shown and described, it is to be understood that the invention is not limited thereto and protection is sought to the broadest extent the prior art allows.

What is claimed is:

1. A closed catheter system for the introduction and placement of a flexible catheter in the lumen of a blood vessel and using the advancement of a wire into said lumen to guide the flexible catheter as said catheter is advanced and positioned in said lumen, said closed catheter system including:

(a) a hollow needle of a determined length and having a sharpened entering end and an exit end;

(b) a hub axially secured and mounted to said needle and positioned at a selected distance from the sharpened end of said needle, this hub having a skirt portion providing an interior cavity which is open to the rear thereof, this hub having a contoured forward end;

(c) a flexible catheter formed with a through bore and slideable on and along the outer diameter of the needle, said catheter having an entering end sized to be easily inserted with the needle into the lumen of the vessel and with the other end of said flexible catheter attached to a hub adapted to be removably mounted on the contoured forward end of the needle hub;

(d) a wire positioned and sized so as to be a slide fit in the bore of the needle, said wire in its initial position permitting blood flow through the needle and into the interior cavity in the hub, this flow indicating penetration of the needle into the lumen of the blood vessel, this guide wire as it is advanced by manipulation to and through the bore of the needle, shutting off the flow of blood through said needle, and, as the wire is advanced, a non-sharpened entering end exits the sharpened end of the needle, this advancing wire caused to follow the path of the lumen of the blood vessel, and (e) a flexible enclosure from lay-flat tubing and having one end attached to the open rer end of the needle hub, this tubing at least partially encapsulating the guide wire, and with the other end of the wire restrained by means at or near the tubing end which is sealed.

2. A closed catheter system as in claim 1 in which the exit end of the needle extends into the skirt portion of the needle hub, said extending portion of the needle having a hole in the side wall of said extending portion, this hole near the needle-securing portion of the needle hub and with the entering end of the wire placed in the exit end portion of the needle sufficiently distant from said hole so that in initial position and condition said wire is not in way of the side hole.

3. A closed catheter system as in claim 2 in which the flexible enclosure is secured to the rear of needle hub with a heat seal.

4. A closed catheter system as in claim 2 in which the flexible enclosure is secured to the rear of the needle hub with adhesive.

5. A closed catheter system as in claim 2 in which the flexible enclosure is secured to the rear of the needle hub with a shrink band.

6. A closed catheter system as in claim 2 in which the distal end of wire has a secured sleeve, with this sleeve secured between said head-sealed end, and with a second heat-seal near the end of the flexible enclosure and to provide securing means for the end of the wire.

7. A closed catheter system as in claim 2 in which the needle hub is a molding of plastic and the skirt portion thereof is at the least translucent.

8. A closed catheter system as in claim 1 in which the needle is secured in the needle hub so that its exit-end portion of the needle terminates at a tapered guideway formed in said needle hub, this tapered guideway adapted to guide the advancing wire into the bore of the needle and with the wire sized to nearly, if not completely, inhibit fluid flow through the needle bore.

9. A closed catheter system as in claim 8 in which the needle hub is formed with a reduced shoulder portion sized to receive and retain the forward end of the flexible enclosure.

10. A closed catheter system as in claim 9 in which the needle hub is a molding of plastic and the skirt portion thereof is at the least translucent.

11. A closed catheter system and device for the introduction and placement of a flexible catheter in the lumen of a blood vessel and using the advancement of an enclosed wire into said lumen to guide the flexible catheter as said catheter is advanced and positioned in said lumen, this device retaining the "feel" properties of an Intravenous catheter without attached guide wire during initial penetration, said closed catheter system including:
   (a) a conventional Intravenous catheter (I.V.) characterized as having:
      (a-1) a hollow needle of a determined length and having a sharpened entering end and an exit end;
      (a-2) a hub axially secured and mounted to said needle and positioned at a selected distance from the sharpened end of said needle, this hub having a skirt portion providing an interior cavity which is open to the rear thereof, this hub having a contoured forward end;
      (a-3) a flexible catheter formed with a through bore and slideable on and along the outer diameter of the needle, said catheter having an entering end sized to be easily inserted with the needle into the lumen of the vessel, and with the other end of said flexible catheter attached to a hub adapted to be removably mounted on the contoured forward end of the needle hub;
   (b) a flexible wire positioned and sized so as to be a slide fit in the bore of the needle of the conventional intravenous cather, said wire in its initial position permitting blood flow through the needle and into the interior cavity in the hub, this flow indicating penetration of the needle into the lumen of the blood vessel, this guide wire as it is advanced by manipulation to and through the bore of the needle, shutting off the flow of blood through said needle, and, as the wire is advanced, a non-sharpened entering end exits the sharpened end of the needle, this advancing wire caused to follow the path of the lumen of the blood vessel, and
   (c) a flexible enclosure from lay-flat tubing and having one end attached to the open rear end of the needle hub, this tubing at least partially encapsulating the guide wire, to achieve a closed system, and with said flexible end enclosure and wire maintaining a balanced catheter when center of gravity is within the confines of the conventional Intravenous catheter so as to be able to "feel" the wire as it is advanced.

12. A method of constructing and using a closed catheter system for the introducing and placing of a flexible catheter in the lumen of a blood vessel and using the advancing of a wire into said lumen to guide the flexible catheter as said catheter is advanced and positioned in said lumen, said construction and use of a closed catheter system including the steps of:
   (a) providing a hollow needle of a determined length and having a sharpened entering end and an exit end;
   (b) axially securing and mounting said needle in a hub and positioning said hub at a selected distance from the sharpened end of said needle, and forming this hub with a skirt portion therewith providing an interior cavity which is open to the rear thereof, and forming this hub with a contoured forward end;
   (c) providing a flexible catheter with a through bore and sized to be slideable on and along the outer diameter of the needle, said catheter having an entering end sized to be easily inserted with the needle into the lumen of the vessel, and securing the other end of said flexible catheter to a hub which is formed to be removably mounted on the contoured forward end of the needle hub;
   (d) furnishing and positioning a wire which is sized so as to be a slide fit in the bore of the needle, said wire in its initial position permitting blood to flow through the needle and into the interior cavity in the hub, indicating by this flow penetration of the sharpened end of the needle into the lumen of the blood vessel, this guide wire as it is advanced, shutting off this flow of blood to and through the bore of the needle, and, as the wire is advanced, a blunt entering end exits the sharpened end of the needle, this advancing wire following the path of the lumen of the blood vessel, and
   (e) securing one end of a flexible enclosure made from lay-flat tubing to the needle hub and arraying this tubing so as to at least partially encapsulate the guide wire while restraining the other end of the wire by means at or near the tubing end which is sealed.

13. A method of constructing and using a closed catheter system as in claim 12 which includes the further step of extending the exit end of said needle into the skirt portion of the needle hub and forming a hole in the side wall of said extending portion, and positioning said hole near the needle-securing portion of the needle hub and placing the entering end of the wire in the exit end of the needle and sufficiently distant from said hole so that in initial position and condition said wire is not in way of said hole.

14. A method of constructing and using a closed catheter system as in claim 13 which further includes securing the flexible enclosure to the rear of the needle hub so as to provide an exclusion of air and the like.

15. A method of constructing and using a closed catheter system as in claim 14 which further includes attaching to the distal end of the wire a sleeve member and securing this end and sleeve between the end seal of the flexible enclosure and a second heat-seal of the enclosure near this distal end of the wire.

16. A method of constructing and using a closed catheter system as in claim 12 including the further step of securing the needle in the needle hub so that the exit end of the needle terminates at an intermediate portion of the needle hub, and forming a tapered recess and guideway whose small end terminates at this exit end of the needle, with this tapered recess providing a guideway for advancing the wire into the bore of the needle and with the wire sized to nearly, if not completely, inhibit fluid flow through the needle bore.

17. A method of constructing and using a closed catheter system as in claim 16 which includes forming the needle hub with a reduced shoulder portion sized to receive the forward end of the flexible enclosure and securing said flexible enclosure end on said reduced shoulder so as to exclude any an all air and the like.

18. A method of constructing and using a closed catheter system as in claim 17 which includes molding the needle hub of plastic which is at the least translucent.

19. A method of constructing and using a closed catheter system and device for the introducing and placing of a flexible catheter in the lumen of a blood vessel and using the advancing of a wire into said lumen to guide the flexible catheter as said catheter is advanced and positioned in said lumen, this device minimizing the weight of the device to provide "feel" during initial penetration, said construction and use of a closed catheter system and device including the steps of:
   (a) providing a hollow needle of a determined length and having a sharpened entering end and an exit end;
   (b) axially securing and mounting said needle in a hub and positioning said hub at a selected distance from the sharpened end of said needle, and forming this hub with a skirt portion therewith providing an interior cavity which is open to the rear thereof, and forming this hub with a contoured forward end;
   (c) providing a flexible catheter with a through bore and sized to be slideable on and along the outer diameter of the needle, said catheter having an entering end sized to be easily inserted with the needle into the lumen of the vessel, and securing the other end of said flexible catheter to a hub which is formed to be removably mounted on the contoured forward end of the needle hub;
   (d) furnishing and positioning a wire which is sized so as to be a slide fit in the bore of the needle, said wire disposed to be advanced by manipulation to and through the bore of the needle and, as the wire is advanced, a blunt entering end exits the sharpened end of the needle, this advancing wire following the path of the lumen of the blood vessel;
   (e) securing one end of a flexible enclosure made from lay-flat tubing, said tubing out to a selected length, with first and second ends open to the rear end of the needle hub and arraying this tubing so as to at least partially encapsulate the guide wire;
   (f) restraining said guide wire within the lay-flat tubing and sealing the second end of this tubing, and
   (g) this flexible end enclosure so designed and of a thickness so as to allow the practitioner to maintain good balance and to "feel" the wire as it is advanced while maintaining sterililty, this wire grasped through the sides of said flexible enclosure near the needle hub and advanced in small increments in and with repeated steps until the desired advancement limit of the wire is reached, and then with manipulation separation of the catheter and its hub from the needle, needle hub, wire and flexible enclosure is achieved and discarding of these separated components is made.

20. A method of constructing and using a closed catheter system and device as in claim 19 in which the forming of the needle hub includes molding the hub of at least translucent materials and with the skirt of the needle having a tapered portion, with the small end of the taper terminating at the exit end of the needle, and with this taper providing a guideway for the wire whose entering end is sized to slide in the bore of the needle and provide inhibiting means for the flow of blood through the bore of the needle.

21. A closed catheter system for the introduction and placement of a flexible catheter in the lumen of a blood vessel and using the advancement of a wire into said lumen to guide the flexible catheter as said catheter is advanced and positioned in said lumen, said closed catheter system including:
   (a) a hollow needle of a determined length and having a sharpened entering end and an exit end;
   (b) a hub axially secured and mounted to said needle and positioned at a selected distance from the sharpened end of said needle, this hub having a skirt portion providing an interior cavity which is open to the rear thereof, the exit end of the needle extending into the skirt portion of the needle hub, said extending portion of the needle having a hole in the side wall of said extending portion, this hole near the needle-securing portion of the needle hub, this hub having a contoured forward end;
   (c) a flexible catheter formed with a through bore and slideable on and along the outer diameter of the needle, said catheter having an entering end sized to be easily inserted with the needle into the lumen of the vessel and with the other end of said flexible catheter attached to a hub adapted to be removably mounted on the contoured forward end of the needle hub;
   (d) a wire positioned and sized so as to be a slide fit in the bore of the needle, said wire disposed to be advanced by manipulation to and through the bore of the needle and, as the wire is advanced, the entering end of said wire is placed in the exit end portion of the needle sufficiently distant from said hole so that in initial position and condition said wire is not in way of the side hole, this wire having a non-sharpened entering end which is disposed to exit the sharpened end of the needle, this exiting-end advancing wire caused to follow the path of the lumen of the blood vessel, and
   (e) a flexible enclosure from lay-flat tubing and having one end attached to the open rear end of the needle hub, this tubing at least partially encapsulating the guide wire, and with the other end of the wire restrained by means at or near the tubing end which is sealed.

22. A closed catheter system as in claim 21 in which the flexible enclosure is secured to the rear of needle hub with a heat-seal.

23. A closed catheter system as in claim 21 in which the flexible enclosure is secured to the rear of the needle hub with adhesive.

24. A closed catheter system as in claim 21 in which the flexible enclosure is secured to the rear of the needle hub with a shrink-band.

25. A closed catheter system as in claim 21 in which the distal end of wire has a secured sleeve, with this sleeve secured between said heat-sealed end, and with a second heat-seal near the end of the flexible enclosure and to provide securing means for the end of the wire.

26. A closed catheter system as in claim 21 in which the needle hub is a molding of plastic and the skirt portion thereof is, at the least, translucent.

27. A method of constructing and using a closed catheter system for the introducing and placing of a flexible catheter in the lumen of a blood vessel and using the advancing of a wire into said lumen to guide the flexible catheter as said catheter is advanced and positioned in said lumen, said construction and use of a closed catheter system including the steps of:
  (a) providing a hollow needle of a determined length and having a sharpened entering end and an exit end;
  (b) axially securing and mounting said needle in a hub and positioning said hub at a selected distance from the sharpened end of said needle, and forming this hub with a skirt portion therewith providing an interior cavity which is open to the rear thereof, and extending the exit end of said needle into the skirt portion of the needle hub and forming a hole in the side wall of said extending portion, and positioning said hole near the needle-securing portion of the needle hub and forming this hub with a contoured forward end;
  (c) providing a flexible catheter with a through bore and sized to be slideable on and along the outer diameter of the needle, said catheter having an entering end sized to be easily inserted with the needle into the lumen of the vessel, and securing the other end of said flexible catheter to a hub which is formed to be removably mounted on the contoured forward end of the needle hub;
  (d) furnishing and positioning a wire which is sized so as to be a slide fit in the bore of the needle, said wire disposed to be advanced by manipulation to and through the bore of the needle, and placing the entering end of the wire in the exit end of the needle and sufficiently distant from said hole so that in initial position and condition said wire is not in way of said hole, and, as the wire is advanced past said hole, the wire shutting off the flow of blood through said needle, and with a blunt entering end of the wire exiting the sharpened end of the needle, this advancing wire following the path of the lumen of the blood vessel, and
  (e) securing one end of a flexible enclosure made from lay-flat tubing to the needle hub and arraying this tubing so as to at least partially encapsulate the guide wire while restraining the other end of the wire by means at or near the tubing end which is sealed.

28. A method of constructing and using a closed catheter system as in claim 27 which further includes securing the flexible enclosure to the rear of the needle hub so as to provide an exclusion of air and the like.

29. A method of constructing and using a closed catheter system as in claim 28 which further includes attaching to the distal end of the wire a sleeve member and securing this end and sleeve between the end seal of the flexible enclosure and a second heat-seal of the enclosure near this distal end of the wire.

* * * * *